United States Patent
Bertha et al.

(10) Patent No.: US 7,648,719 B2
(45) Date of Patent: Jan. 19, 2010

(54) METHOD FOR OXYGEN TREATMENT OF UNSATURATED CARBON COMPOUNDS, NOVEL EPOXY-STRUCTURED MATERIAL OBTAINED BY THE METHOD, APPARATUS FOR CARRYING OUT THE METHOD AND A THERAPEUTIC COMPOSITION USING THE MATERIAL

(75) Inventors: Andras Bertha, Hermann Otto u. 32, Budapest (HU) 1026; Mihaly Lantos, Lepke u. 32., Budapest (HU) 1026; Peter Kolta, Pecs (HU); Peter Kolta, legal representative, Nagymezo u. 58., Budapest (HU) 1065; Gergely Kolta, Nagymezo u. 45., Budapest (HU) 1065

(73) Assignees: Peter Kolta, Budapest (HU); Gergely Kolta, Budapest (HU); Andras Bertha, Budakeszi (HU); Mihaly Lantos, Budapest (HU)

( * ) Notice: Subject to any disclaimer, the term of this patent is extended or adjusted under 35 U.S.C. 154(b) by 726 days.

(21) Appl. No.: 10/497,582

(22) PCT Filed: Dec. 4, 2002

(86) PCT No.: PCT/HU02/00135

§ 371 (c)(1),
(2), (4) Date: Nov. 29, 2004

(87) PCT Pub. No.: WO03/047630

PCT Pub. Date: Jun. 12, 2003

(65) Prior Publication Data

US 2005/0226944 A1    Oct. 13, 2005

(30) Foreign Application Priority Data

Dec. 4, 2001    (HU)    .................................. 0105252
Dec. 4, 2001    (HU)    .................................. 0105253

(51) Int. Cl.
*A61K 36/47*    (2006.01)
*A61K 36/55*    (2006.01)
*A61K 36/00*    (2006.01)
*A61K 36/28*    (2006.01)

(52) U.S. Cl. ...................... 424/731; 424/764; 424/768; 424/769

(58) Field of Classification Search .................. 424/731, 424/764, 769, 768; 549/523
See application file for complete search history.

(56) References Cited

U.S. PATENT DOCUMENTS 5,183,911 A * 2/1993 Washuttl et al. ............. 554/181
5,292,941 A * 3/1994 Kigawa et al. ............... 562/544

FOREIGN PATENT DOCUMENTS

DE            911884      6/1959
EP            0346189     6/1989
WO            WO 0220502  9/2001

* cited by examiner

Primary Examiner—James O Wilson
Assistant Examiner—Ebenezer Sackey
(74) Attorney, Agent, or Firm—Anthony H. Handal; Thompson Hine LLP (57) ABSTRACT

Method for oxygen treatment of liquid unsaturated carbon compounds with carbon number between 6 and 26 wherein the material is placed in a reaction chamber (11), a mixture ozone and oxygen is passed through the material, and by controlling the flow rate of the gas mixture through the material the temperature of the reaction is controlled to remain below a predetermined maximum value being 100° C. As a result of the reaction a novel material is obtained which has an epoxy-structure, has a higher density and smaller viscosity than the starting material, it has excellent burning properties and can be used as a limited rate source of oxygen. The apparatus for carrying of the method comprises an oxygen source, and ozonizer (6), a reaction chamber (11) for containing the liquid starting material, a gas pump (13) for removing the gas from the reaction chamber, and a temperature control system. An expedient field of application for the novel material is a therapeutic composition that facilitates natural metabolism of cells that comprises hydroxy proline and a neutral carrier material, wherein the amount of the material is below 20% and the amount of hydroxy proline is below 10%.

6 Claims, 5 Drawing Sheets

METHOD FOR OXYGEN TREATMENT OF UNSATURATED CARBON COMPOUNDS, NOVEL EPOXY-STRUCTURED MATERIAL OBTAINED BY THE METHOD, APPARATUS FOR CARRYING OUT THE METHOD AND A THERAPEUTIC COMPOSITION USING THE MATERIAL

In EP 0 822 807 B1 a composition is described for therapeutic, veterinary and cosmetic applications that comprises the most important components required for the metabolism of living cells, ie. oxygen and proline or hydroxy proline. The effect lied in that at locations of burns or mechanical injuries, where capillaries, that have the task of transporting blood, have got injured, the natural healing process has started in spite of the locally insufficient blood supply. The unique wound healing effect was demonstrated by experiments described in detail.

In that composition oxygen was present under a pressure substantially higher than normal atmospheric one, and the applied gelatine carrier was used to bound oxygen after having cooled down and became stiffer due to the high surface tension of the gel, whereby oxygen was present in the form of microscopic tiny bubbles. The difficulty in using such a composition lied in that the increased pressure had to be maintained till the moment of actual use. This condition could be solved by the use of specific double walled containers. A further difficulty lied in that a covered treatment was recommended in order to divert oxygen towards the injured surface. Covered treatments are known to be complex, which limits the possible applications.

A further problem was that under the effect of the high pressure oxygen the proline content of gelatine got transformed into hydroxy proline that made the consistency of the gel more watery and liquid reducing thereby the surface tension, which lead to increased escape loss of oxygen.

The main objective of the present invention is to provide a new material which has increased oxygen content and which can act as an oxygen generator in several fields of applications.

A further object is to provide a method of making the new material and an apparatus for carrying out the method.

A still further object is to provide a composition for therapeutic, veterinary and cosmetic applications, which can utilise the effects obtained by the above referred EP patent, wherein the oxygen carrier material can replace the oxygen carrier of gelatine under high pressure.

For solving the above objectives a starting material had to be found which is tissue friendly and can be used also for therapeutic applications.

According to the invention it has been found that unsaturated carbon hydrogens with carbon number between 6 and 26 tend to capture oxygen in an epoxy structure when treated with ozone or a mixture of ozone and oxygen if the temperature of the treatment is controlled not to exceed a maximum threshold value, which is about 100° C. and more preferable at most 80° C.

The most appropriate materials are natural plant oils or oleic acid, and of the plant oils the best results are obtained by using olive oil, castor oil, sunflower oil or linseed oil.

The method for preparing the novel composition comprises uses liquid unsaturated carbon compounds having carbon number between 6 and 26, and comprises the steps of placing the liquid material to be treated in a reaction chamber at a temperature of at most 40° C., passing a mixture of ozone and oxygen gas through the liquid in the reaction chamber, continuously measuring the temperature of the liquid, continuing said passage at least until the measured temperature has reached a maximum value, controlling the temperature in the reaction chamber during the passage of the gas mixture below 100° C. by reducing the rate of flow of the mixture, whereby a different material is obtained from the liquid starting material that has an epoxy structure and a higher specific density and smaller viscosity.

It is preferable if the maximum temperature is set to 80° C.

An expedient field of application for this novel material lies in a composition for therapeutic, veterinary and cosmetic application, comprising hydroxy proline, and a carrier material, which comprises this epoxy-structured novel material as an oxygen carrier an amount less than 20 mass percent, preferably between about 5 and 10%.

The metabolism will be facilitated if the composition comprises vitamin C in granulated form, wherein the particles being covered by a layer resistive against the other components in the composition but nonresistive to plasma liquids present in living tissues.

The apparatus for carrying out the method comprises a high voltage ozonizer having a regulated ozone outflow line; a reaction chamber having an inflow and an outflow duct, the inflow duct is connected to the outflow line of the ozonizer and comprises a filter element permeable for the inflowing gas but non-permeable for the starting liquid material, the reaction chamber contains the starting liquid material; a gas pump coupled to the outflow duct of the reaction chamber, a thermometer measuring the temperature of the liquid material; and a temperature regulator connected to the thermometer and coupled to the ozonizer to reduce or cut off gas supply if the temperature exceeds a predetermined maximum.

The apparatus comprises preferably a vapor binding means connected in the input gas supply line of the ozonizer to reduce vapor in the supplied gas.

It is also preferable if the gas pump has a controllable gas flow rate for adjusting the speed of reaction.

The novel material has expedient properties, it is more dense and has less viscosity than the starting material, tests have proven that the material can deliver oxygen to neighbouring materials and has excellent burning properties.

The listed primary, field of application can be regarded as one of several applications yet to be found.

The invention will now be described in connection with preferable embodiments and examples, wherein reference will be made to the accompanying drawings.

Figure 1:
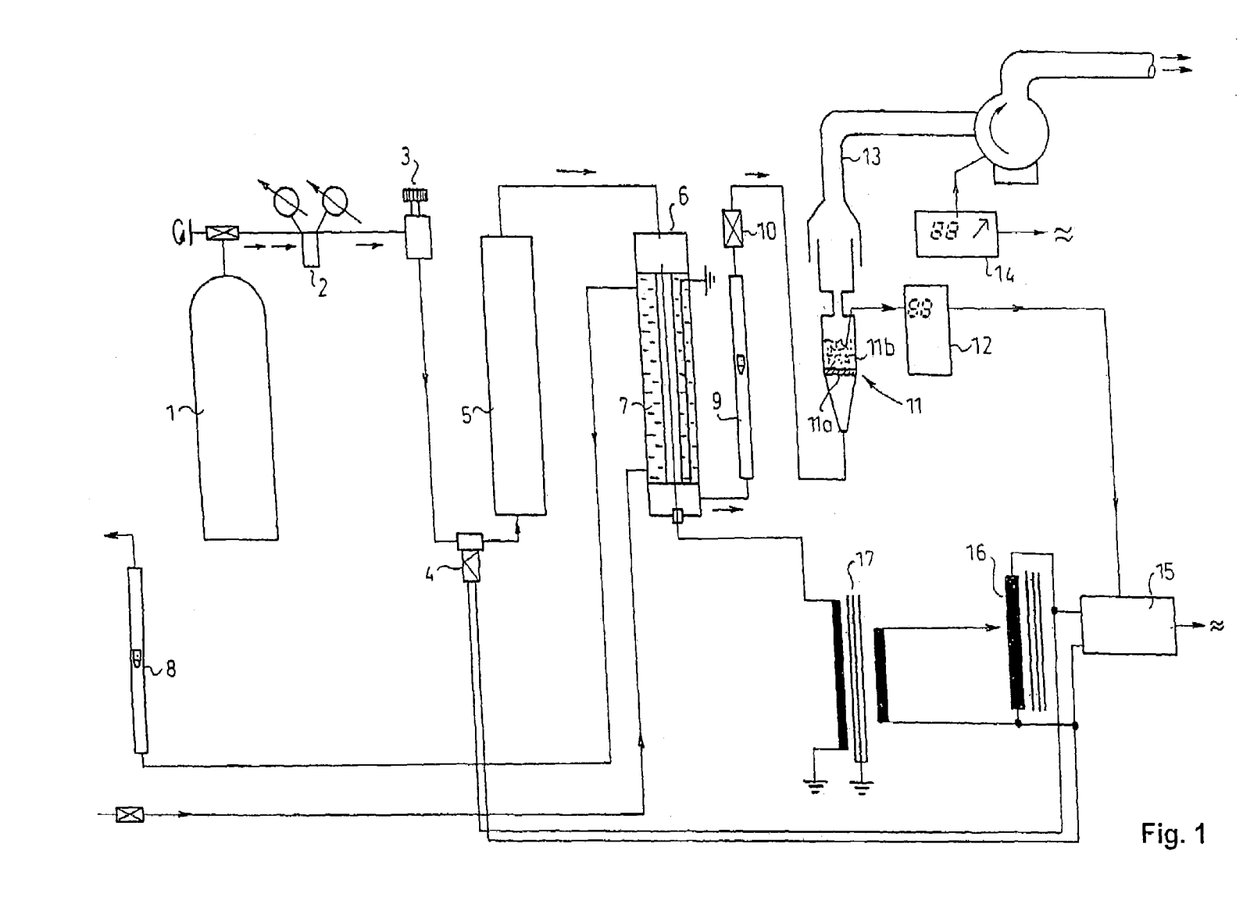
FIG. 1. shows the schematic arrangement of the apparatus used for making the novel material with epoxy-structure.

The ozone generator unit of the ozone treatment apparatus shown in FIG. 1 comprises an oxygen container 1 with high pressure, a pressure reducer 2 having preferably a multi stage design and being connected to the container 1, a pressure regulating valve 3 inserted in the outflow branch of the reducer 2, furthermore a magnetically controlled closing valve 4, a column 5 filled preferably with silica-gel for reducing the amount of vapor present in the initial oxygen gas; and a high voltage ozonizer 6. The ozonizer 6 is constituted by a cylindrical column made of an insulating material preferably glass or ceramic. The column comprises a high voltage electrode extending along the central axis thereof surrounded by a cylindrical cooling sleeve 7 spaced therefrom in radial direction, in which a cooling medium, preferably water is flown. The flowing rate of the cooling medium is indicated by rotation type flow meter 8. The glass column of the ozonizer 6 is electrically connected to the earth and this encircles the outer part of the cooling sleeve 7. One end of the cylindrical space surrounding the electrode is coupled to the gas outflow line of the column 5, and the other end is connected through a rotational type gas flow meter 9 indicating the flow rate of the gas and a safety stop check valve 10 to reaction chamber 11.

In the reaction chamber 11 filter element 11a blocks the path of the inflowing gas, and the other side of the filter element 11a contacts and holds the material 11b that takes part in the reaction, which is constituted in the exemplary embodiment by olive oil. The pore size of the filter element 11a lies between 20-100 μm, thus the inflowing gas can freely flow through the pores. At the given pressure (being atmospheric or close thereto) the filter is non permeable for the material 11b having a high viscosity and being in liquid or gel state, therefore the material 11b cannot enter the gas system preceding the reaction chamber 11. The reaction chamber 11 and the filter element 11a can be made preferably from a commercially available filter funnel provided with a porous glass filter, wherein the diameter of the filter disc is 90 mm, and the space above the filter is about 500 ml. It is advantageous if a second, somewhat larger reserve space is provided beyond the reaction chamber 11, where the material obtained in the reaction and taking possibly a foam-like form can collect. The temperature of the material 11b present in the reaction space of the reaction chamber 11 is measured by a thermometer 12 that has a fast response and having preferably a digital design, and the temperature output of the thermometer 12 forms the basic signal for controlling the reaction, and this output is coupled to the input of an emergency stop system 15.

The reaction chamber 11 and the storage space above it are open, and a gas release ventilation system 13 ending in a funnel removes all outflowing gas. Flow regulator 14 controls the flow rate of the system 13. The ventilation system 13 comprises furthermore an ozone neutralising (heater) column (not shown in the drawing) that prevents the gas flowing to the air from comprising ozone exceeding a predetermined permitted threshold level.

The high voltage electrode of the ozonizer 6 is coupled to high voltage output of a high voltage transformer 17 that has a primary winding coupled through a toroid transformer 16 and the protective stop system 15 to the line voltage. By adjusting the voltage of the toroid transformer 16 the intensity of the discharge in the ozonizer 6 can be changed. The control input of the protective stop system 15 is connected to the output of the thermometer 12 that supplies a voltage when the sensed temperature exceeds a predetermined maximum limit value. In such occasions the protective stop system activates the closing valve 4, too.

The apparatus shown in FIG. 1 is used for producing from unsaturated carbon compounds with carbon atom number falling between 6 and 26 and having a specific density lower than unity, constituted preferably by natural plant oils a material that captures oxygen by epoxy bond. One of the appropriate materials for this purpose is the commonly used olive oil (oleum olivae), which in a purified form constitutes a registered pharmaceutical base material. The olive oil used for the experiments had the pharmaceutically required purity, and it had a density of 0.8333 g/cm$^3$, it had a slightly yellowish color and its viscosity did not differ from that of olive oils used in normal households.

In the system shown in FIG. 1 30 ml olive oil was placed on the filter element 11a of the sterilised reaction chamber 11 before the operation was started. Prior to the application of the high voltage, the cooling of the ozonizer 6 has to be started, i.e. cooling water is circulated in the cooling sleeve 7 and the temperature of both the inflowing and outflowing water are measured. As a second step the fan in the ventilation system 13 was started, and by opening the pressure regulating valve 3 pure oxygen gas was introduced in the system. The toroid transformer 16 was switched on line voltage, and a voltage level was adjusted in the ozonizer 6, which can produce a sufficiently high electrical field to partially convert the inflowing oxygen gas into ozone. The reaction generates heat, which is removed by the cooling water. In normal operation a temperature difference of about 8-10° C. should be adjusted between the inflowing and outflowing water. The silica gel present in the column 5 ensures that vapor concentration in the oxygen gas flowing into the ozonizer 6 remains below 0.01 ppm. This is required because a substantially higher vapor content could noticeably worsen the efficiency of ozone formation or could even prevent ozone generation.

If the voltage is sufficiently high for ozone formation, the amount of ozone flowing through the reaction chamber 11 is determined predominantly by the position of the regulating valve 3. The capillaries in the filter element 11a uniformly distribute the gas (being a mixture of oxygen and ozone) entering the reaction chamber 11. The gas flows through the liquid layer thereabove in the form of bubbles, and it contacts the liquid along a high surface area through the whole cross section, and a reaction will take place between the gas and the liquid. This reaction is associated with intensive generation of heat. With regard to this fact the reaction temperature should be kept below a permitted predetermined threshold value by controlling the amount of ozone supply. According to our experiments the maximum temperature should be lower than 100-105° C.

For that purpose the output of the thermometer 8 coupled to the stop system 15 is activated when a temperature of 80° C. is reached, and in that case the stop system 15 switches off the high voltage and breaks the oxygen supply by means of the closure valve 4. It is preferably if during such an emergency stop the closing valve closes the oxygen supply, and passes a neutral gas i.e. nitrogen to the input of the system, so that the cool neutral gas can terminate any ongoing reaction. The operation of the ventilation system 13 is continuously sustained, and attention is paid to maintain this continuity.

During the reaction the distribution of the gas flowing through the oil mass can be changed by the adjustment of the speed of the fan in the ventilation system 13. It has been experienced that optimum circumstances take place if a toroid-like formation is established on the free oil surface. As the reaction goes on, the viscosity of the oil decreases, and the preservation of this toroid formation requires the increase of the fan speed. The storage space above the reaction chamber 11 is required for security reasons only. If the initial ozone flow is too strong, the oil volume is increased accompanied by an intensive foam formation, and the excess storage space is required for receiving this increased oil volume. With suitably adjusted operational parameters this foam formation and volume increase cannot take place.

Figure 2:
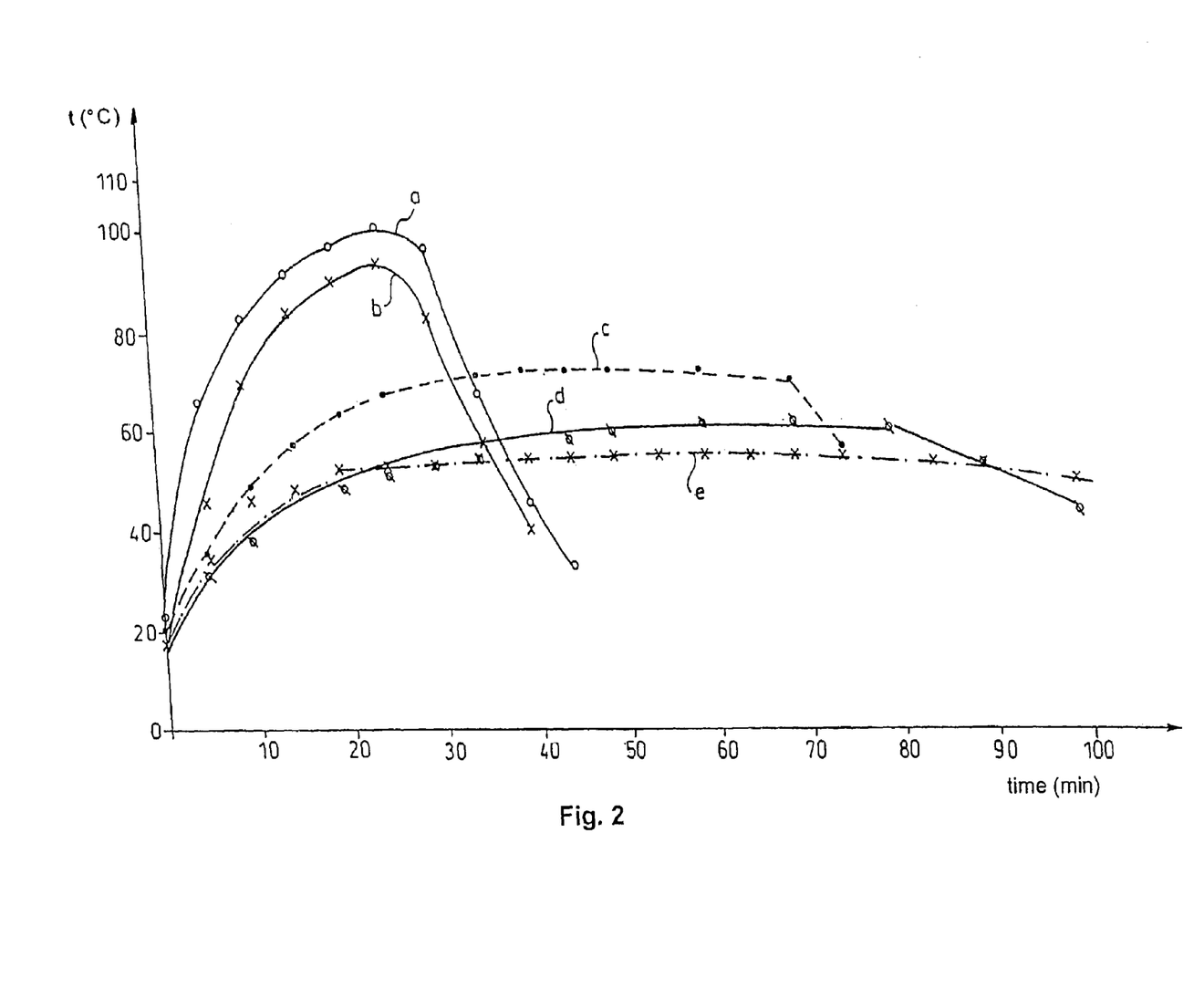
FIG. 2 show the time diagram of the reaction temperature at different gas flow rates.

The temperature-time curves of the reaction between the initial olive oil and ozone are shown in the diagrams of FIG. 2. The difference between the respective curves lies in the position of the pressure-regulating valve 3, the gas flow was the highest at diagram a and the smallest at diagram e. The initial temperature increase, then after reaching a maximum the slow decrease is characteristic to all of the curves. According to our hypothesis regarding the nature of the reaction, during the curve section that lasts till the maximum, one of the double bonds interconnecting the carbon chains in the starting material gets split and by means of its two valence an oxygen atom will be built in one of the bonds, which is characteristic to epoxy bonds. This is an exothermal process that causes the initial increase in temperature. After the maximum temperature has been reached, the temperature continuously decreases. It is supposed that this process takes place in case of olein, which constitutes a substantial portion (about 70%) of olive oil by the epoxidation of the double bond between the $9^{th}$ and $10^{th}$ carbon atom, i.e. triolein epoxide is formed.

If the gas supply is maintained till the material cools down to room temperature, then the structure of the material obtained will remain stable through a long period of time. It can be seen in the curves of FIG. 2 that by decreasing the gas supply the reaction gets slower and the maximum becomes more flat. Although the properties of the materials obtained by the process according to any of diagrams a. to e. did not change noticeably, the material was most stable when the maximum temperature lied between 60 and 80° C.

Figure 3:
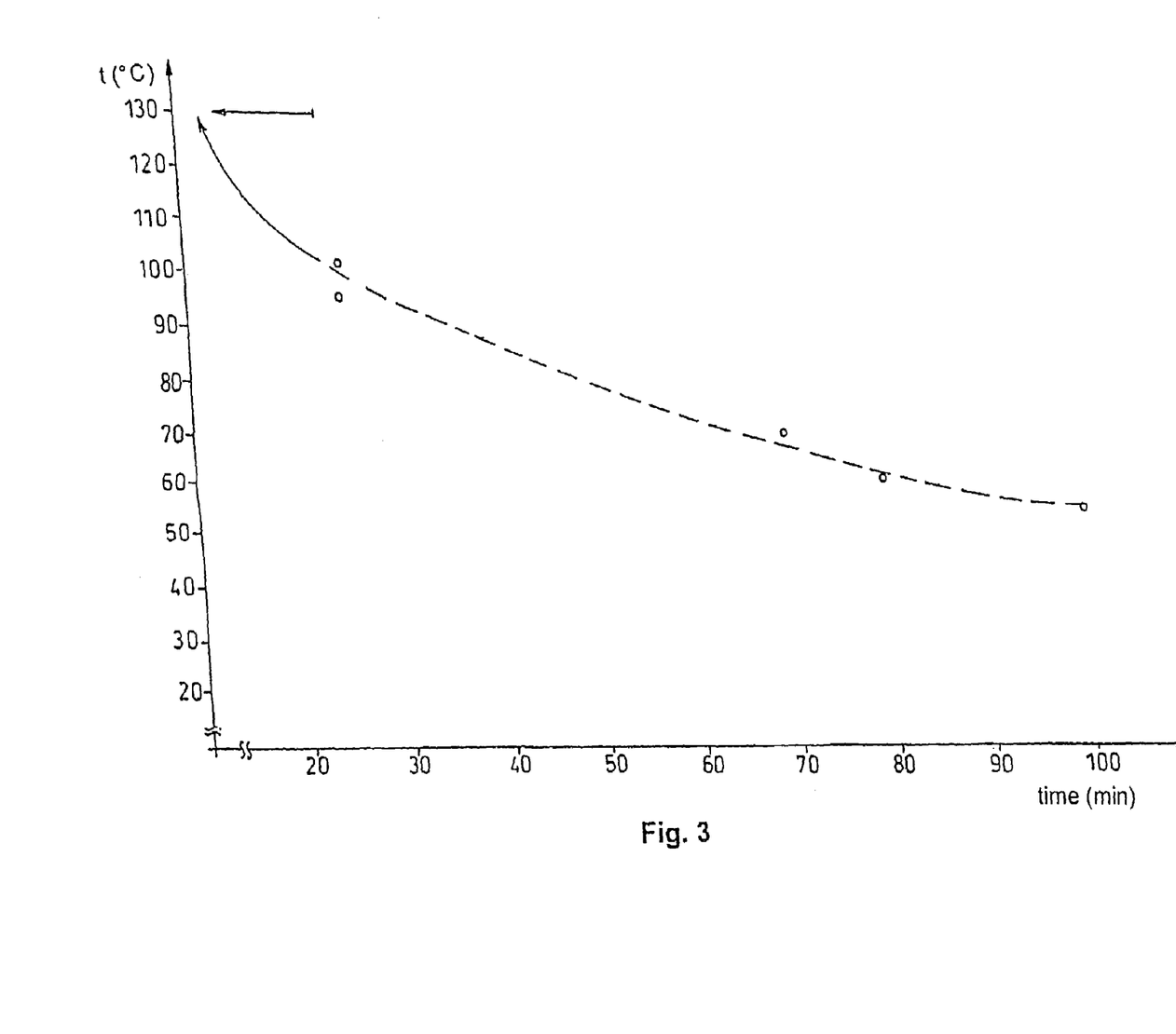
FIG. 3 shows the peak temperatures of the reaction with the associated time data taken with different gas flow rates.

FIG. 3 shows the maximum temperatures and the time required for reaching the associated maximums in case of processes that take place with different reaction speeds. The diagram is therefore not continuous, each point is associated with data of distinct reactions carried out with different ozone flow. The dashed curve illustrates the stable range of reaction without any self-reaction.

The material obtained as a result of the stable reaction has properties substantially differ from those of the initial oil. From the yellowish, transparent, well-flowing olive oil a milk-white material is obtained that has a substantially lower viscosity, in a test tube it looks-like as if it were solid, in a pot it hardly flows. After the material has been taken out of the reaction chamber its measured density was 1.082 $g/cm^3$. The material had a smell characteristic otherwise to electric arc discharges.

The material comprises substantial amount of bound oxygen. A small amount of spontaneous oxygen discharge is also characteristic to the material that can be intensified by creating appropriate ambient conditions (e.g. when contacting tissues being poor in oxygen. Such a condition can further be e.g. if the material contacts a damp environment, wherein the partial oxygen pressure is substantially lower. In the material with epoxy structure the partial pressure of oxygen corresponds to normal atmospheric pressure, which is about five times as high as the partial oxygen pressure in free air being about 0.2 bar.

For illustrating the phenomenon of spontaneous oxygen release the change of the weight of 1 ml material was measured in the first 50 hours after it has been prepared. The data are summarised in the following table:

|  | t (hours) | | | | | | |
| --- | --- | --- | --- | --- | --- | --- | --- |
|  | 0 | 1 | 2 | 4 | 5 | 6 | 50 |
| mass (g) | 1.082 | 1.081 | 1.0805 | 1.080 | 1.0795 | 1.079 | 1.0565 |

For the sake of comparison the spontaneous loss of weight of the initial olive oil was also measured. The starting weight of 1 ml olive oil was 0.8722 g, which decreased by the end of the first hour to 0.8715 g and this value has remained the same also by the end of the $50^{th}$ hour. It is supposed that the initial loss of mass could have been the result of the release of a slight amount of volatile components. The comparative examination shows that the mass of the treated material decreases in time monotonously but with decreasing slope.

Figure 4:
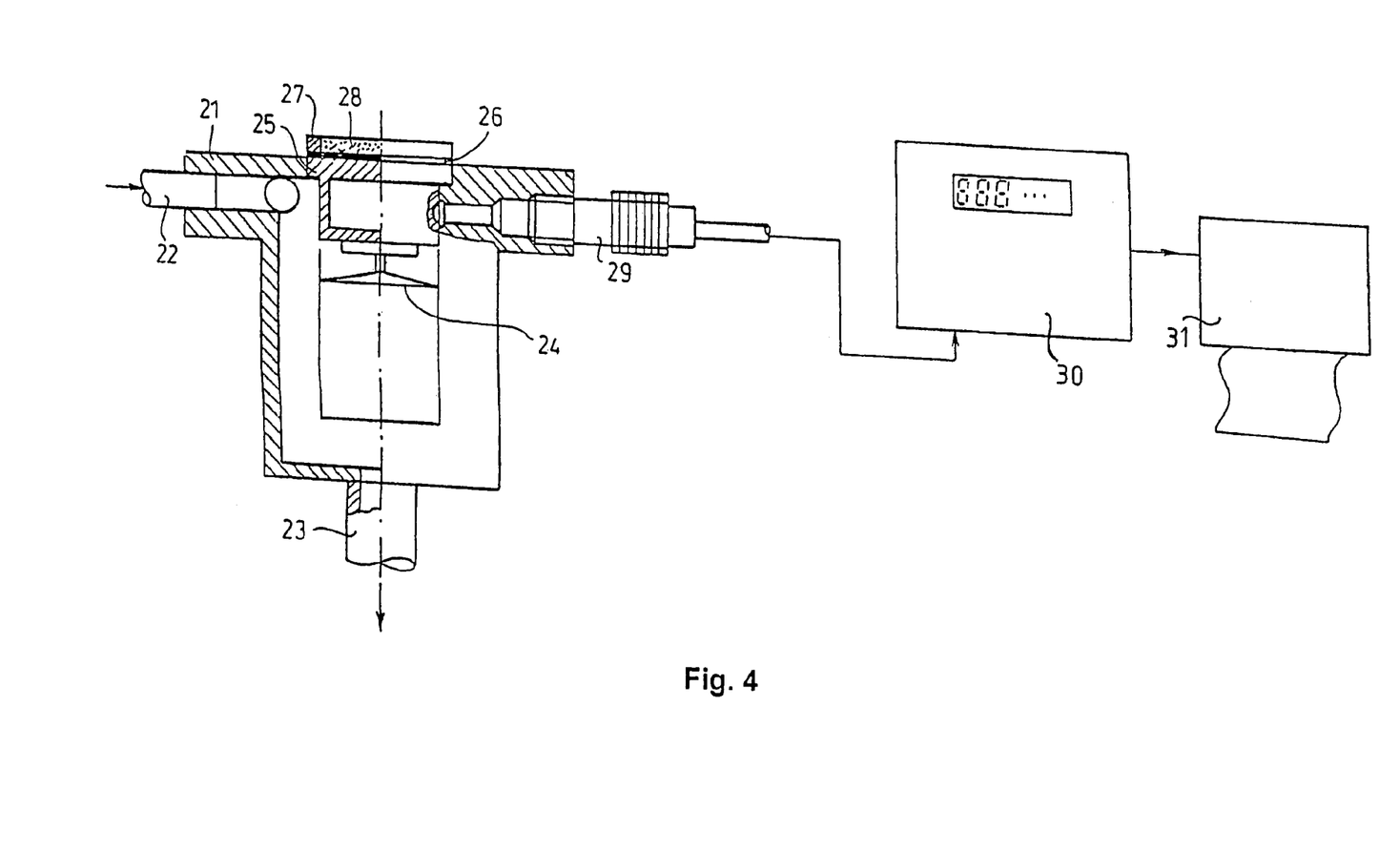
FIG. 4 shows a schematic measurement system used for determining oxygen delivery.

In addition to the density measurements the oxygen release and oxygen content has, been measured directly by means of the measuring arrangement shown in FIG. 4. In the arrangement the Chemical Microsensor instrument labelled by reference numeral 30 and manufactured by Diamond General Company, U.S.A. was used with a sensing probe 29 of the Clark electrode type and a plotter 31. In the hollow interior of a chamber 21 used for the measurements the temperature was kept at 32° C. with an accuracy of 0.5° C. The temperature stabiliser water enters through inflow conduit 22 in the chamber 21 and it is discharged through conduit 23. In the interior of the chamber 21 a measuring container 25 is arranged that constitutes an accessory of the instrument 30 and it has an inner space of 0.8 $cm^3$ volume, and a nest is provided in the side wall of the container 25 for receiving the sensing probe 29. The measuring container 25 is filled with a physiologic saline solution, which is continuously nixed by a magnetic mixer 24. The free upper surface of the measuring container 25 is covered by membrane 26 made of a PVC film with a thickness of 9 μm and kept by the pressing force of ring 27 abutting the stable rim of the chamber 21. The interior of the ring 27 was filled with experimental material 28 to be measured. It was supposed that in case of oxygen release by the material 28 oxygen will be diffused through the membrane 26 in the saline solution present in the container 25, and the probe 29 will detect this oxygen.

Figure 5:
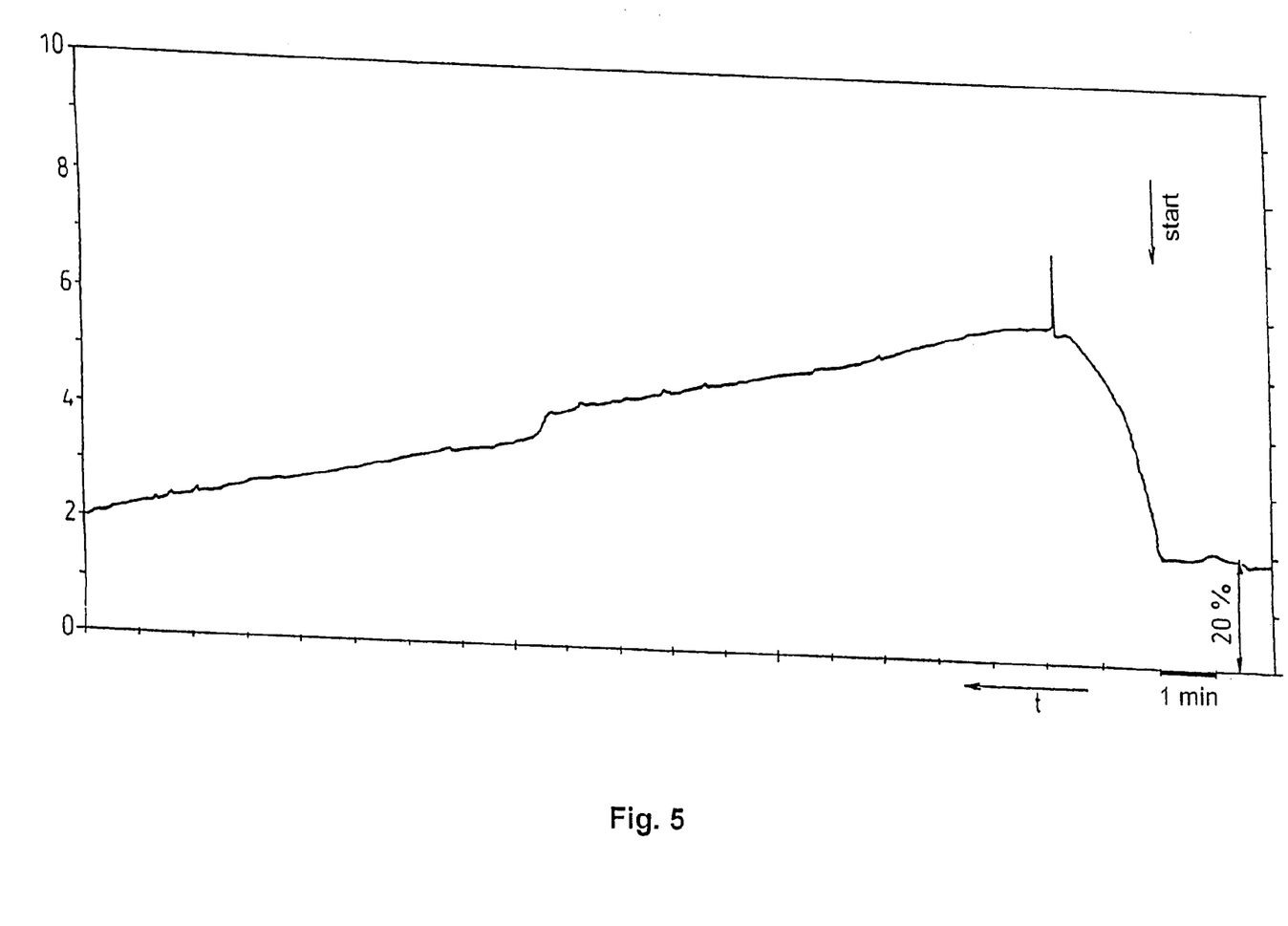
FIG. 5 shows a diagram taken by the system of FIG. 4.

FIG. 5 shows the curve as obtained by the plotter 31 which has a time axis increasing from left to right. From the initial value of 20% the measured oxygen concentration increased to nearly three times as high, then the high amount of oxygen present gradually consumed the activity of the Clark electrode and in this range the measured signal returned to the initial state. The valuable data here are comprised in the initial region of the jump, furthermore the oxidation of the Clark electrode confirms that sufficient amount of oxygen was present in the solution. The measurements were repeated by freshly activated Clark electrodes after the experimental material 28 was stored at free air for seven and eight days, respectively, and the diagrams obtained were similar to the one shown in FIG. 5.

When the material is stored in a closed space, e.g. in a jar or in a tube, or it is mixed with an additive that forms a thin film on the outer surface with a thickness of few microns, these alternative conditions can prevent the spontaneous oxygen release. In such cases the material will preserve its ability of releasing oxygen through a long period of time.

In case of the example shown the structural change of the initial olive oil of 30 ml volume took place in 45 minutes, and this requires a flow of ozone containing gas of 25 l/hour. In the exemplary case the associated energy consumption was 200-250 W.

The formation of epoxy structure has been examined in case of other oils, too.

The chosen starting material was oleic acid (acidum oleum) having a pharmaceutically required purity of which a volume of 20 ml was placed in the reaction chamber 11. The flow rate of the gas mixture of ozone and oxygen was 120-130 l/hour. By means of the toroid transformer a primary voltage of 200V was applied on the primary winding of the high voltage transformer 17. The temperature T of the reaction space is given as a function of time of treatment in table 2.

TABLE 2

Oleic acid

| t (h, min) | T (° C.) |
|---|---|
| 0 00 | 24.1 |
| 0 15 | 56.7 |
| 0 30 | 66.5 |
| 0 45 | 69.6 |
| 1 00 | 70.6 |
| 1 15 | 71.8 |
| 1 30 | 73.6 |
| 1 45 | 75 |
| 2 00 | 76.0 |
| 2 15 | 76.8 |
| 2 30 | 77.0 |
| 2 45 | 77.0 |
| 3 00 | 77.0 |
| 3 15 | 76.0 |
| 3 30 | 74.7 |
| 3 45 | 72.3 |
| 4 00 | 67.7 |
| 4 15 | 58.8 |
| 4 30 | 46.5 |

During the treatment the colour of the material has started becoming yellowish after 50 minutes, by the end of the first hour it has taken a color between orange and red currant, it has become gradually darker and by the end of the second hour it was coffee brown, about 2 hours and 30 minutes foam started to build at the top and it became dark purple and by the end of the fourth hour it became black. After it has cooled down to room temperature, the density was 1.42 g/cm³ and it had a dense, sticky consistency. The material was burning fast with a blue, almost UV color flame.

In a further experiment the rate of ozone generation was decreased and a voltage of 140 V was applied to the primary winding of the high voltage transformer 17, all other parameters were identical. As a result the temperature rose slower and by the end of the first hour it has taken only 58° C.

The reaction was made by using sunflower oil (oleum heliante) having a pharmaceutically required purity. The adjusted parameters were: volume of the material under test was 30 ml, it had an initial density of 0.92 g/cm³, the primary voltage was 150V, and the flow rate of the gas mixture was 120 l/hour. The values of the temperature T as a function of time are summarized in table 3.

TABLE 3

Sunflower oil

| t (h, min) | T (° C.) |
|---|---|
| 0 00 | 21.8 |
| 0 10 | 56.0 |
| 0 20 | 65.3 |
| 0 30 | 66.0 |
| 0 40 | 64.0 |
| 0 50 | 61.4 |
| 1 00 | 60.5 |
| 1 10 | 59.6 |
| 1 20 | 58.7 |
| 1 30 | 58.2 |
| 1 40 | 58.2 |
| 1 50 | 58.2 |
| 2 00 | 58.3 |
| 2 10 | 56.8 |
| 2 20 | 54.1 |
| 2 30 | 47.7 |
| 2 40 | 39.6 |
| 2 50 | 33.0 |

During the reaction foam was not formed, the material has taken after 20 minutes a light white color. After cooling down to room temperature its density was 1.17 g/cm³. It burned with a huge yellow flame. The consistency of the material was gel-like and substantially more dense than sunflower oil.

The reaction was made by using pure linseed oil (oleum lini). The adjusted parameters were: volume of the material under test was 30 ml, it had an initial density of 0.925 g/cm³, the primary voltage was 160V, and the flow rate of the gas mixture was 120 l/hour. The values of the temperature T as a function of time are summarized in table 4.

TABLE 4

Linseed oil

| t (h, min) | T (° C.) |
|---|---|
| 0 00 | 19.5 |
| 0 10 | 48.0 |
| 0 20 | 54.0 |
| 0 30 | 55.0 |
| 0 40 | 53.0 |
| 0 50 | 52.6 |
| 1 00 | 51.3 |
| 1 10 | 49.8 |
| 1 20 | 49.0 |
| 1 30 | 47.7 |
| 1 40 | 42.5 |
| 1 50 | 38.2 |

During the reaction an intensive foam formation was observed around the 10$^{th}$ minute and by about the 20$^{th}$ minute the foam collapsed. Following the 30$^{th}$ minute the material started becoming more dense, following the 40$^{th}$ minute the reaction temperature quickly decreased, and the passage of the ozone-oxygen mixture was terminated at 1 hour and 50 minutes, and thereafter the material cooled down to room temperature. The epoxy-structured material had a gel-like consistency, its density at 20° C. was 1.16 g/cm³. It burned intensively with a yellow flame.

The reaction was made by using castor oil (oleum ricini) having a pharmaceutically required purity. This material is one of the most dense plant oil (density lies between 0.9 and 0.96 g/cm³). The adjusted parameters were: volume of the material under test was 30 ml, it had an initial density of 0.925 g/cm³, the primary voltage was 100V, and the flow rate of the gas mixture was 120 l/hour. The values of the temperature T as a function of time are summarized in table 5.

TABLE 5

Castor oil

| t (h, min) | T (° C.) |
|---|---|
| 0 00 | 20.0 |
| 0 10 | 52.5 |
| 0 20 | 63.5 |
| 0 30 | 55.0 |
| 0 40 | 43.0 |
| 0 50 | 36.8 |
| 1 00 | 31.0 |
| 1 10 | 26.0 |

During the reaction foam was not formed, however, the generation of heat was very intensive, the reaction was fast and the temperature maximum was reached already by the 20$^{th}$ minute. During the reaction it appears that not only the epoxy structure has been formed but also a polymerisation has taken place because after cooling down the material had a jelly-like consistency and it hardens with temperature. It is not soluble in any usual solvent other than ketones. We could not determine its density because after solidifying gas islets formed in the material that made usual density-measuring methods inapplicable. The color of the material was similar to that of milk with an opalescent character.

Of the unsaturated carbon compounds of natural plant origin coconut oil was the last under examination. This material is a widely used cosmetic base material, at room temperature its consistency is similar to that of fat. Because the bubbling through by gas requires a liquid carrier material, the reaction was started at 36° C. temperature at which coconut oil has taken a sufficiently liquid form. The measured density of the starting material was 0.969 g/cm$^3$. The amount of material in the reaction was 30 ml, the primary voltage was set to 200V. The values of the temperature T as a function of time are summarized in table 6.

TABLE 6

| Coconut oil | |
|---|---|
| t (h, min) | T (° C.) |
| 0 00 | 36.0 |
| 0 05 | 64.0 |
| 0 10 | 59.0 |
| 0 15 | 51.0 |
| 0 20 | 39.5 |
| 0 40 | 34.8 |
| 0 50 | 32.5 |
| 1 00 | 32.0 |

During the reaction a sudden and fast rise in temperature was experienced, the temperature maximum 64° C. was reached in the 5$^{th}$ minute, thereafter the temperature rapidly fell. Around the 10$^{th}$ minute a granulation started, which lasted till the end of the reaction. Following the reaction the measured density was 0.994 g/cm$^3$.

Following the experiments with unsaturated plant oils and fats we wished to determine in an experimental way, whether the above described epoxy formation and exothermic reaction are the exclusive properties of unsaturated carbon derivatives or similar reactions take place in case of saturated oils. Repeated experiments were carried out with silicon oil, paraffin oil and with neutral oil listed in the pharmacopoeia (oleum neutrale). These oils comprise saturated oils only. During the reaction respective samples of 30 ml volume were taken and the mixture of ozone and oxygen was passed through each of them. The primary voltage was 200V and the flow rate was 120 l/h. At these listed oils neither increase in temperature nor more than 1% increase in density were found. Based on these result it can be correctly stated that exothermal reaction resulting in a structural change can be experienced only in case of starting materials with unsaturated roots.

The material prepared in the described way that captures oxygen with an epoxy bond has proven as an efficient oxygen source, which property can be utilized in a number of fields.

One of such expedient fields is constituted by the improvement of the cream designated by the name PROLOXIN described in the above referred publications that comprises gelatine and oxygen under high pressure.

The metabolism of cells requires the presence of nutrition and oxygen, and when any problem occurs in the supply of such materials, a local imbalance will take place. In case of burns, mechanical injuries, frost penetration and bedsore (decubitus) the blood supply in the injured areas is obstructed or insufficiently provided. The PROLOXIN material comprised oxygen and hydroxyproline required for the building up of the cells, and in the simultaneous presence of these components several examples for the fast, uniform and scar-free healing were demonstrated. When the gel was prepared oxygen was supplied directly, at a pressure exceeding the atmospheric one. On the contrary, hydroxyproline was not supplied directly, it was created from one component of gelatine i.e. from proline in the presence of oxygen.

We have supposed that the above-described olive oil with epoxy structure can provide the required oxygen, and this supply does not require the application of a pressure higher than the atmospheric one. This carrier oil is a material listed in the codex of registered drugs, it does not harm health and it can be simply mixed with hydroxy proline, with known neutral gel or cream-foaming materials and in case of need with other additives to form a preparation having the required consistence.

For verifying the above outlined supposition preclinical examinations were carried out with New-Zealander rabbits. We have examined the simultaneous effects of the oxygen-carrier base-material prepared from olive-oil as a first component and hydroxy-proline as a second component in case of two different concentrations of the second component, by using first a usually applied cream base material and second a usual gel-base. A further test was also made for the purpose of comparison using a gel prepared from gelatine saturated with high-pressure oxygen.

Short Description of the Preclinical Examinations

The experimental animals were New-Zealander rabbits with weight between 2.5 to 3 kg. The animals were individually placed in standard non-corrodible cages with grated floor. Planing chipping constituted the bedding. The temperature in the animal house was 18±2° C., and in every 10 minutes the air was freshened and changed. The relative humidity was 65-80%. Standard rabbit feed was used for the feeding, the animals were given as much tap water as they wanted.

Two days before the treatment the hair was cut from the back region of the animals between the shoulder and pelvic lines by a cutting-machine and the residual hair was removed by cosmetic epilation. The skin surface was washed by lukewarm water then dried followed by a rest of 24 hours.

Before the treatment the animals were assigned in six groups, each containing five animals and each animal was treated as follows:

Automatic heated stamps with an area of 2 cm$^2$ and having a temperature of 182±2° C. was used to create burn injuries of third order. The stamp was applied on the bare hairless skin surface (having an area about 12×8 cm) in two diametrically opposing locations for respective 15 seconds duration. At the two other diametrically opposite locations of the same skin areas the skin was scratched in a depth reaching till the interstitial tissues under the skin.

The skin surface of each animal was treated daily twice with a material associated with the group concerned. The animals in a control group were also treat twice a day with a hydrophilic base cream without any active ingredient. The macroscopic changes i.e. the extent of healing were observed and recorded every other day.

On the 9$^{th}$ day in case of each animal a tissue sample was taken by biopsy for histological examination from one of the four wounded areas, and the biopsy was repeated when the animals were considered to have healed.

The cut skin samples were fixed in a neutral 3% formalin solution and were taken for histological examination.

The treatment of the respective groups was as follows:
I. Hydrophilic cream according to PH. Hg. VII with 3% hydroxyproline content;
II. Hydrophilic cream according to PH. Hg. VII with 5% hydroxyproline content;
III. Wet gel according to PH. Hg. VII with 5% hydroxyproline content;
IV. Wet gel according to PH. Hg. VII with 10% hydroxyproline content;
V. Control group; and
VI. Gel as described in the cited US patent enriched with pressurised oxygen with 5% gelatine content.

In each of the material used in groups I to IV the amount of olive oil treated to have an epoxy structure was 10%. The hydroxyproline applied was manufactured by the French Company REXIM belonging to the Degussa-Hüls group and it was L-hydroxy-proline. The abbreviation PH. Hg. VII relates to the $7^{th}$ edition of the official Hungarian codex of pharmaceuticals, named Pharmacopea Hungarica, in which the listed drugs generally correspond to the ones used in the codex of the EU states.

In the groups I and II the cream base material was unguentum hydrophylicum non-ionicum as defined in Ph. Hg. VII which is a non-emulsive, nonionic cream. The cream comprised additionally 5% glycerine and 2% solutio conservant. The listed components (including the required amount of hydroxyproline) were mixed together and with the required amount of distilled water at a temperature of 40° C., and a white cream was obtained.

In the groups III and IV a gel was made from 10% hydroxy ethyl cellulose by the addition of distilled water, then 5% glycerine, 10% olive oil with epoxy structure and 2% conserving agent in the form of solutio conservant were added. In all examples the amounts expressed in percentages relate to the percent of mass of the associated component in the final product.

Results:

In the first five days of the experiments the following differences were observed with respect to the control group.

In the animals of the groups II, III and IV in the burned areas the usual thickened, scabby and hard layer was not formed, in these groups the burned skin surface retained its flexibility in a more or less way. The macroscopic picture was yellow-white by colour, wet, slightly covered by fibrin, and the area was well distinguishable from the healthy surface.

On the $9^{th}$ day a state definitely different compared to all other groups was observed at two animals in the group III. At both of these animals as a definite sign of healing the above described thin, non-scabby, yellow-white pergameneous layer that covered the burnt area peeled off, and it uncovered a healthy skin surface underneath without visible cicatrices.

On the $11^{th}$ day the skill surface of three animals healed, by the $13^{th}$ day all animals in group III showed this healed picture.

In the control group the complete healing occurred by the $19^{th}$ day. While the healing at the animals of group III was free of cicatrices, the hair grew out, in the control group on the healed surface large scary, hairless spots were observed.

The results at group VI were between those of group III and the control group.

The results of the histological examinations supported the macroscopic observations, the fastest improvement was experienced at group III. The effect manifested itself not only in the quicker healing, but in the uniform healing along the whole wound area. The uniformity of the process resulted in that the healed wound surface has become uniform, almost identical with the healthy skin surface. These properties could be observed both at the burns of third order and at the healing of mechanically caused scratched wounds.

Due to the shown properties the products used in the groups I to IV are appropriate for medical, veterinary applications and also for direct applications in the field of cosmetics, as well as for uses as a base material for different cosmetic products.

In case of very large burns, especially at the beginning of the treatment, the wound cannot be exposed to the mechanical load constituted by the application of the gel or cream. In such cases it can be preferable to male a product with higher viscosity that flows almost like a liquid that can be applied as a spray or foam without mechanically loading the target area. Such a liquid product can be prepared also from the product used in group III, if the amount of hydroxy ethyl cellulose is decreased until the required viscosity is obtained. As the healing process goes on, the treatment can gradually be changed to gel products with smaller viscosity.

The preclinical examinations described above were repeated with compositions comprising epoxy-structured materials made from oleic acid and from castor oil, respectively, whereas the other components were selected as those in group III of the afore described preclinical test. The only difference compared to the previous experiments lied in that instead of the epoxy-structured olive oil the oxygen carrier was a similar epoxy-structured oleic acid respectively castor oil.

The experiments gave results very similar to those described in connection with group III. This means that the specific type of the epoxy-structured carrier has no decisive role in the system.

A still fisher set of preclinical experiments of the same type was carried out, in which the control group obtained the same conventional treatment as in case of the first preclinical test, the first treated group comprised the same composition as used in Group III; and the second treated group used the same composition as the first treated group plus a small concentration of C-vitamin granules covered with a hard gelatine layer. The covered granules were obtained from commercially available vitamin capsules using the commercial name: CeTeBe. The hard gelatine cover prevents vitamin C granules from being oxidized in the ambient medium comprising excess oxygen. During the treatment the gelatine layer got dissolved in the plasma liquid present at all wound areas, and the metabolic process is facilitated by the catalytic presence of vitamin C. The results of the experiments demonstrated in case of the second treated group a definitely faster and better healing compared to the results obtained with the first treated group.

The invention claimed is:

1. Method for oxygen-treatment of liquid unsaturated carbon compounds having a carbon number between 6 and 26, comprising placing the liquid material to be treated in a reaction chamber at an initial temperature of at most in a range around 40° C., passing a mixture of ozone and oxygen gas having an inflow temperature of at most around 40° C. through the substantially full volume of said liquid in the reaction chamber with a substantially uniform rate of flow that substantially increases the temperature of said liquid due to the reaction between said mixture and said liquid, measuring said increasing temperature of said liquid, controlling the temperature in said reaction chamber below a temperature no greater than around 100° C., and terminating said passage of said mixture of ozone and oxygen after said measured temperature reaches the threshold value no greater than around 100 degrees centigrade necessary to convert said unsaturated carbon compounds to an epoxy structure whereby from said starting liquid material a different material is created that has an epoxy structure and a higher specific density and smaller viscosity.

2. The method as claimed in claim 1, wherein said starting liquid material is a plant oil or oleic acid.

3. The method as claimed in claim 2, wherein said plant oil is olive oil, linseed oil, sunflower oil or castor oil.

4. The method as claimed in claim 1, wherein during said controlling step the rate of flow of said mixture and/or the ratio of ozone to oxygen is reduced.

5. Method for oxygen-treatment of liquid unsaturated carbon compounds having a carbon number between 6 and 26, comprising placing the liquid material to be treated in a reaction chamber at an initial temperature of at most in a range around 40° C., passing a mixture of ozone and a substantially dry gas having an inflow temperature of at most around 40° C. through the substantially full volume of said liquid in the reaction chamber with a substantially uniform rate of flow that substantially increases the temperature of said liquid due to the reaction between said mixture and said liquid, measuring said increasing temperature of said liquid, controlling the temperature in said reaction chamber to be below a temperature roughly around 100° C. by varying the amount of ozone passed through the volume of said liquid, and terminating said passage of said mixture of ozone and substantially dry oxygen after said measured temperature reaches the threshold value necessary to convert said unsaturated carbon compounds to an epoxy structure whereby from said starting liquid material a different material is created that has an epoxy structure and a higher specific density and smaller viscosity.

6. The method as in claim 5, wherein the dry gas is oxygen and said measured temperature is allowed to reach and exceed the threshold value necessary to convert said unsaturated carbon compounds to an epoxy structure.

* * * * *